United States Patent
Velasco et al.

(10) Patent No.: US 9,610,193 B2
(45) Date of Patent: Apr. 4, 2017

(54) FORWARD FLOW IMPEDING INFUSION SLEEVE AND ASSOCIATED SYSTEMS AND METHODS

(71) Applicant: Novartis AG, Basel (CH)

(72) Inventors: Kristine Velasco, Foothill Ranch, CA (US); James Y. Chon, Irvine, CA (US)

(73) Assignee: Novartis AG, Basel (CH)

( * ) Notice: Subject to any disclaimer, the term of this patent is extended or adjusted under 35 U.S.C. 154(b) by 556 days.

(21) Appl. No.: 14/097,329

(22) Filed: Dec. 5, 2013

(65) Prior Publication Data

US 2015/0157502 A1 Jun. 11, 2015

(51) Int. Cl.
A61B 17/20 (2006.01)
A61F 9/007 (2006.01)
A61M 3/02 (2006.01)
A61M 1/00 (2006.01)

(52) U.S. Cl.
CPC ....... *A61F 9/00745* (2013.01); *A61M 1/0084* (2013.01); *A61M 3/0216* (2014.02); *A61M 3/0279* (2013.01); *A61M 3/0283* (2013.01); *A61M 2210/0612* (2013.01)

(58) Field of Classification Search
CPC ......... A61M 2210/0612; A61M 3/0283; A61F 9/00745
See application file for complete search history.

(56) References Cited

U.S. PATENT DOCUMENTS

| | | | |
|---|---|---|---|
| 5,030,210 A * | 7/1991 | Alchas | A61M 25/0075 604/247 |
| 5,084,009 A * | 1/1992 | Mackool | A61M 1/0084 604/22 |
| 5,188,589 A | 2/1993 | Wypych et al. | |
| 5,282,786 A | 2/1994 | Ureche | |
| 5,354,265 A | 10/1994 | Mackool | |
| 5,417,654 A | 5/1995 | Kelman | |
| 5,505,693 A | 4/1996 | Mackool | |
| 5,634,912 A | 6/1997 | Injev | |
| 5,645,530 A | 7/1997 | Boukhny et al. | |
| 6,013,046 A | 1/2000 | Maaskamp et al. | |
| 6,039,715 A * | 3/2000 | Mackool | A61F 9/00745 604/22 |
| 6,340,355 B1 | 1/2002 | Barrett | |
| 6,605,054 B2 * | 8/2003 | Rockley | A61F 9/00745 604/22 |
| 7,014,629 B2 | 3/2006 | Mackool | |
| 7,094,229 B2 | 8/2006 | Boukhny et al. | |
| 7,276,060 B2 | 10/2007 | Madden | |

(Continued)

*Primary Examiner* — Phillip Gray

(57) ABSTRACT

An infusion sleeve for use in partially covering a phacoemulsification tip during a surgical operation is disclosed herein. The infusion sleeve includes a flexible elongate portion having a lumen extending therethrough with the phacoemulsification tip running through the lumen. The flexible elongate member further includes a lateral port configured on a side of the flexible elongate member, a straight section, and a tapered section. The tapered section is located at a distal portion of the flexible elongate member and has a first wall subsection having a uniform thickness and a second wall subsection having thickness larger than the uniform thickness. The second wall subsection flexes to maintain circumferential contact with the phacoemulsification tip.

20 Claims, 8 Drawing Sheets

(56) References Cited

U.S. PATENT DOCUMENTS

| | | |
|---|---|---|
| 7,967,775 B2 | 6/2011 | Hong |
| 8,267,891 B2 | 9/2012 | Dimalanta et al. |
| 8,423,126 B2 | 4/2013 | Mackool |
| 2005/0277897 A1 | 12/2005 | Ghannoum et al. |
| 2006/0047241 A1 | 3/2006 | Boukhny |
| 2006/0052758 A1* | 3/2006 | Dewey ................ A61F 9/00745 604/272 |
| 2007/0260173 A1 | 11/2007 | Boukhny et al. |
| 2008/0125699 A1* | 5/2008 | Davis .................. A61M 1/0084 604/35 |
| 2011/0319810 A1 | 12/2011 | Ghannoum |
| 2012/0157934 A1 | 6/2012 | Liao et al. |
| 2013/0102955 A1* | 4/2013 | Koplin ................ A61F 9/00745 604/22 |
| 2014/0052053 A1 | 2/2014 | Hong et al. |
| 2014/0257172 A1 | 9/2014 | Yalamanchili |
| 2015/0112356 A1 | 4/2015 | Chon et al. |
| 2015/0157501 A1 | 6/2015 | Bourne et al. |

* cited by examiner

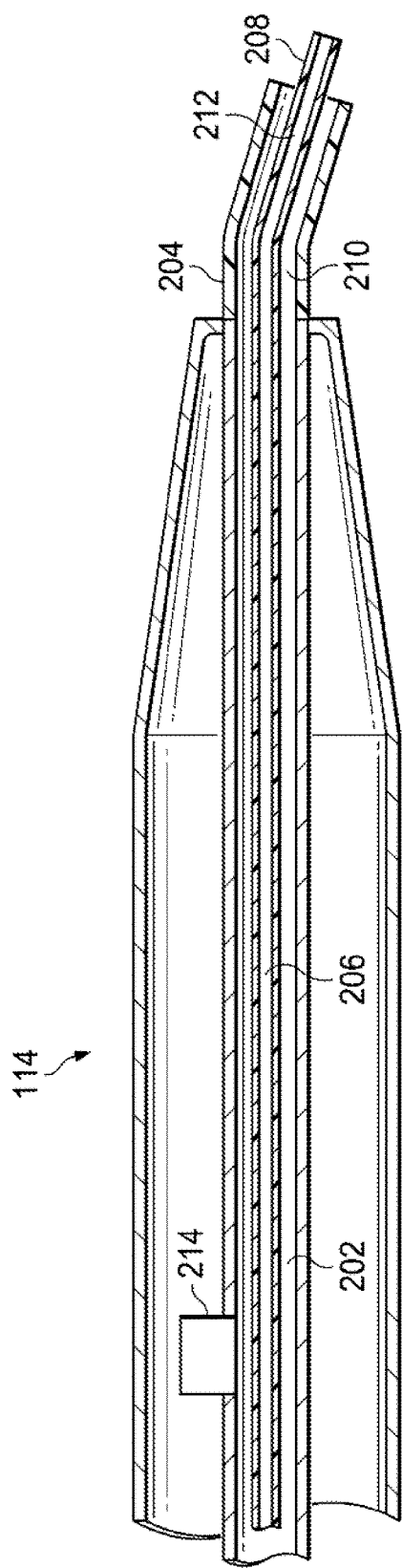
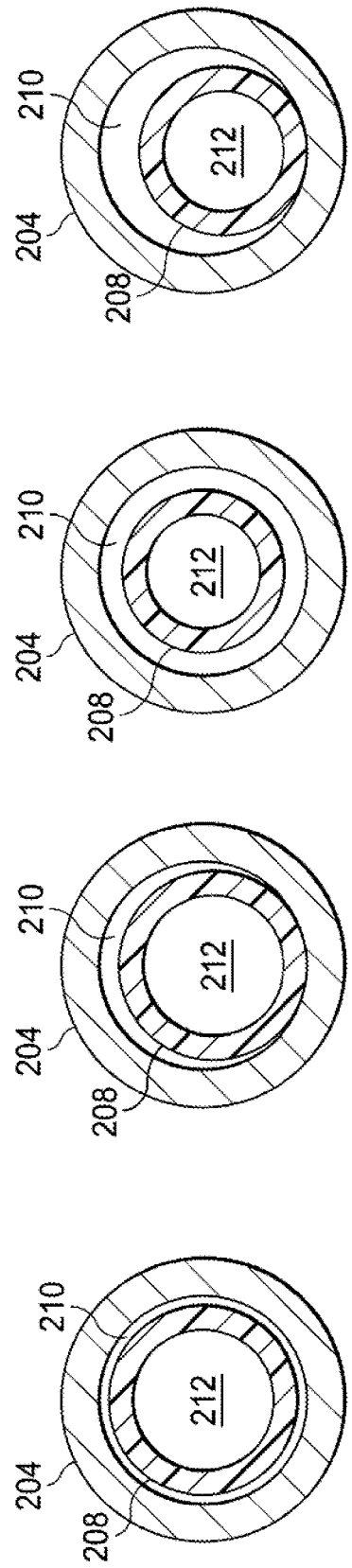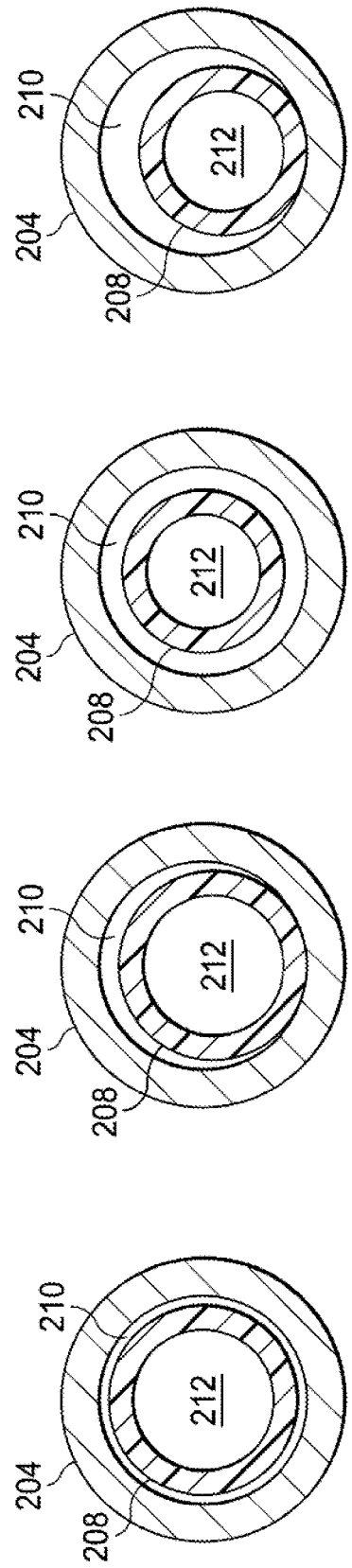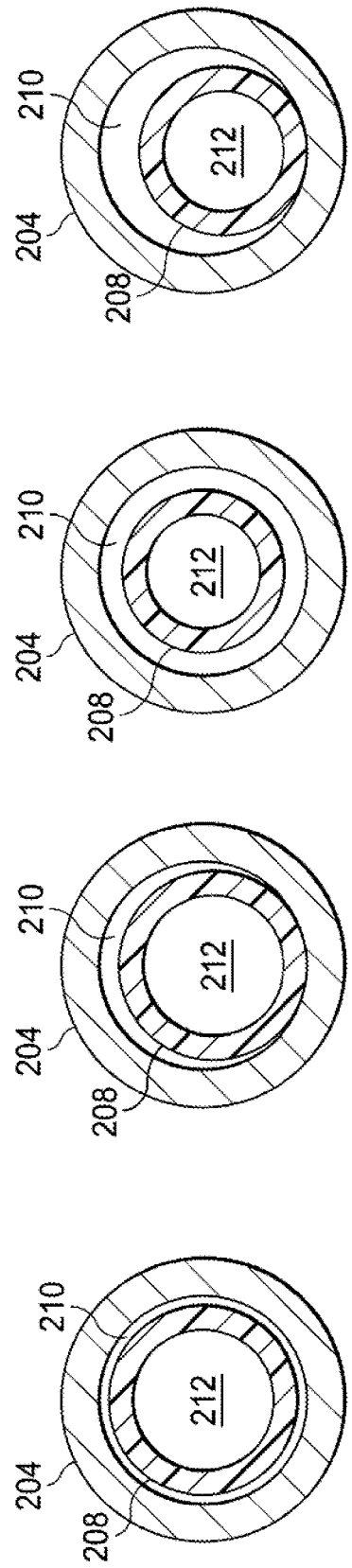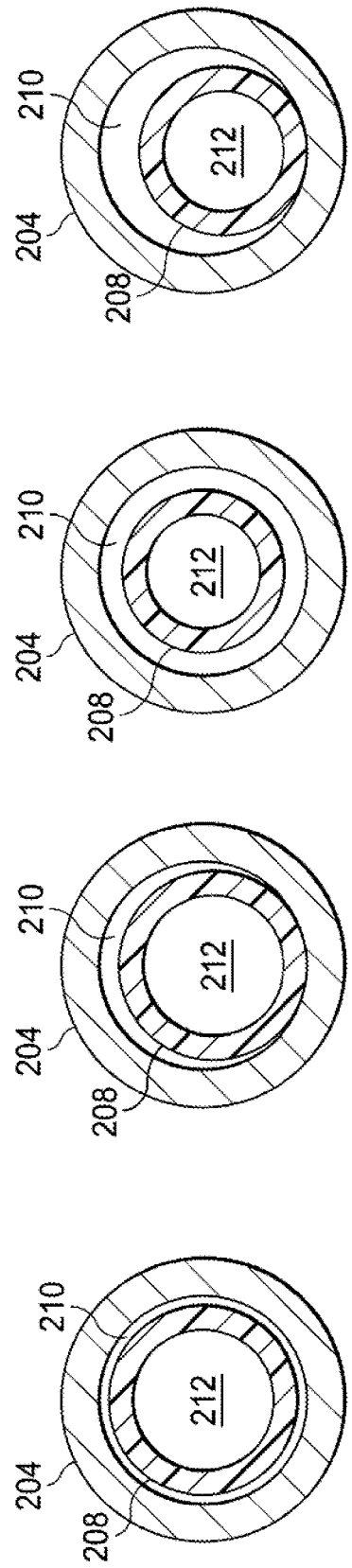

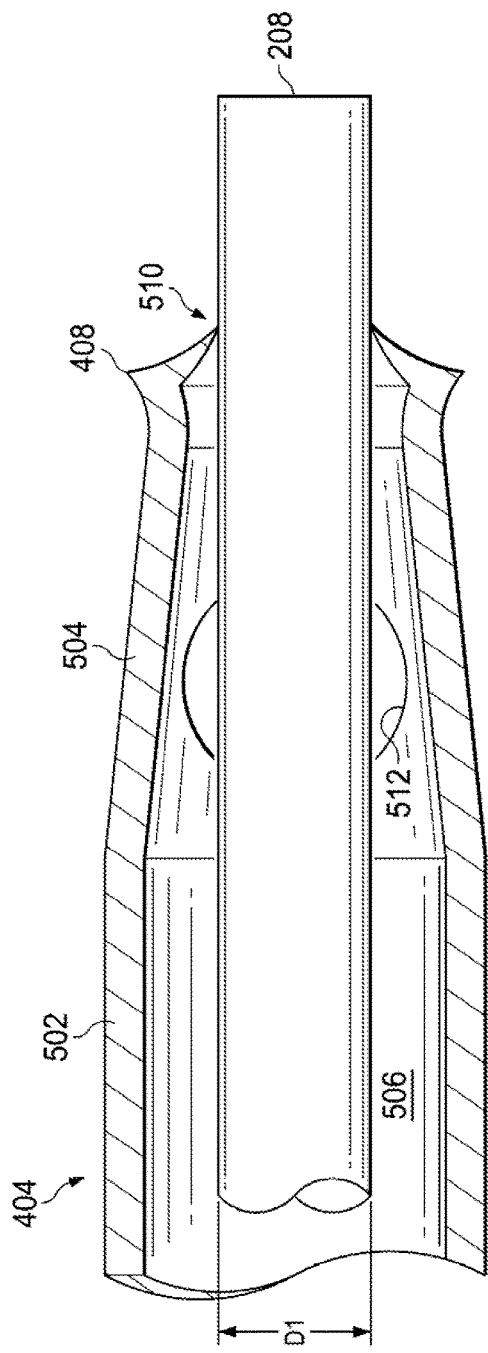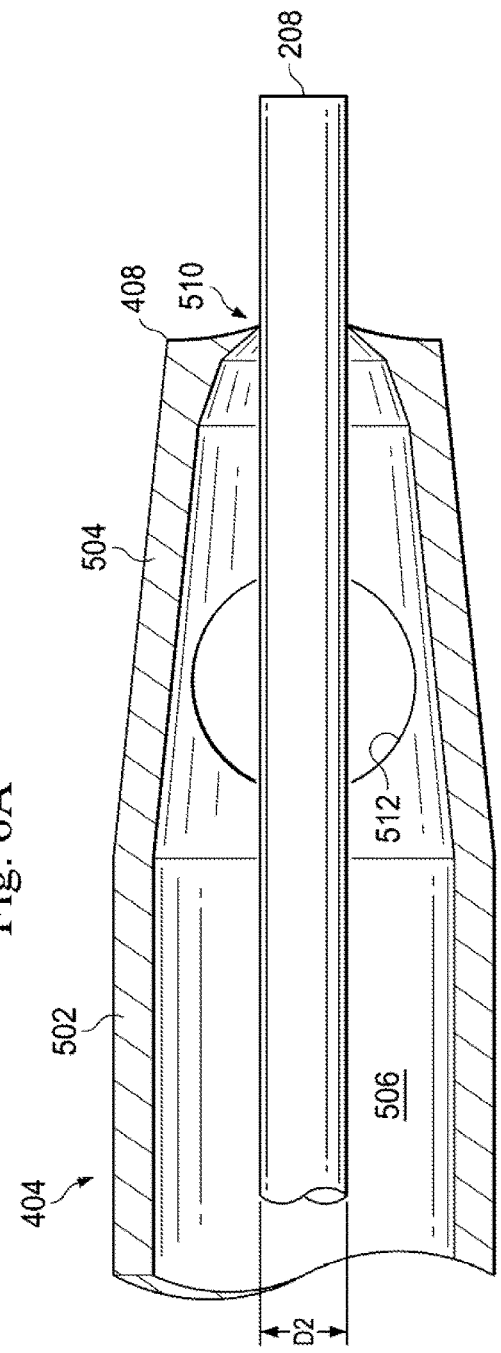
Fig. 6A
Fig. 6B

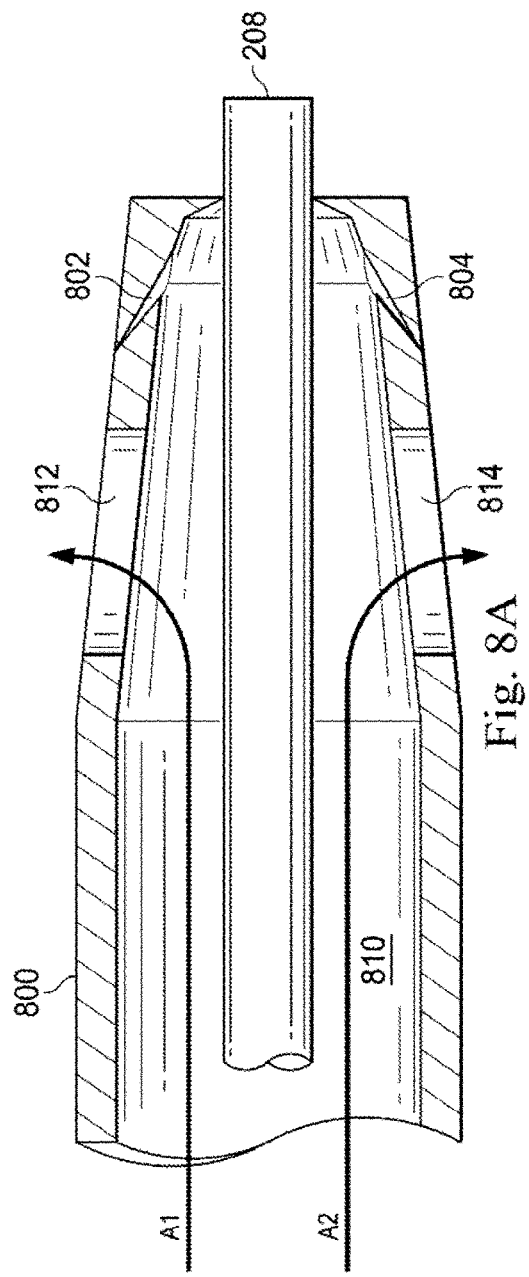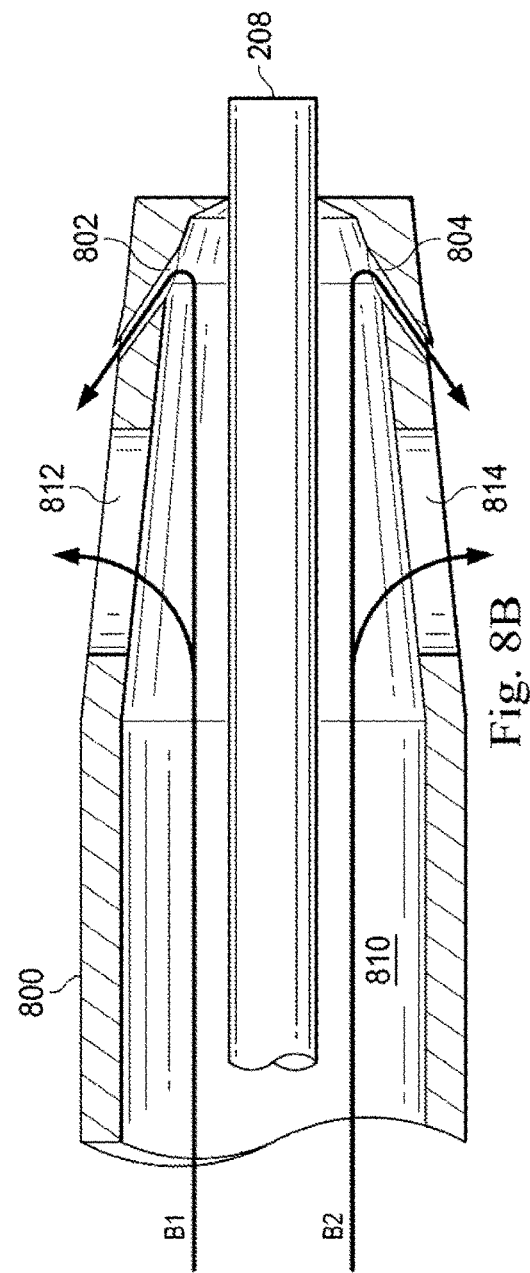

FORWARD FLOW IMPEDING INFUSION SLEEVE AND ASSOCIATED SYSTEMS AND METHODS

BACKGROUND

The present invention relates to systems and methods as used in phacoemulsification procedures, and more particularly, to irrigation or infusion sleeves that position over a phacoemulsification tip during such procedures.

Typical surgical instruments suitable for phacoemulsification procedures on cataractous lenses include an ultrasonically driven phacoemulsification hand piece with a cutting phacoemulsification ("phaco") tip or needle and an irrigation sleeve, and a control console. The hand piece is attached to the control console by an electric cable and flexible tubing. The flexible tubing supplies irrigation fluid to the surgical site and also carries aspiration fluid from the surgical site to a waste or discard reservoir.

During a phacoemulsification procedure, the tip of the cutting phaco needle and the end of the irrigation sleeve are inserted into the anterior segment of the eye through a small incision in the eye's outer tissue. The surgeon brings the tip of the cutting phaco needle into contact with the lens of the eye, so that the vibrating tip fragments the lens. The resulting fragments are aspirated out of the eye through the interior bore of the cutting phaco needle.

Throughout the procedure, irrigating fluid is infused into the eye, passing between the infusion sleeve and the tip of the cutting phaco needle and exiting into the eye at the tip of the infusion sleeve and/or from one or more ports or openings formed into the infusion sleeve near its end. This irrigating fluid prevents the collapse of the eye during the removal of the emulsified lens, protects the eye tissue from the heat generated by the vibrating of the ultrasonic cutting phaco needle, and suspends the fragments of the emulsified lens for aspiration from the eye.

Particularly with small and/or bent phaco tips, such as 20 gauge, the irrigating fluid may exit through a distal end of the infusion sleeve. This is referred to as forward flow. Significant forward flow of irrigating fluid from the infusion sleeve may reduce the performance of the phaco tip, may impact the surgical efficiency, and may result in less than optimal clinical outcomes. Current approaches to reducing forward flow have been unsatisfactory in a number of ways. Therefore, there remains a need for an improved system for reducing or preventing forward flow during a medical procedure. The present disclosure is directed to addressing one or more of the deficiencies in the prior art.

SUMMARY

In one exemplary aspect, the present disclosure is directed to an infusion sleeve for use in partially covering a phaco tip during a surgical operation. The infusion sleeve includes a flexible elongate member having a lumen extending therethrough with the phaco tip running through the lumen. The flexible elongate member further includes at least one lateral port configured on a side of the flexible elongate member, a straight section, and a tapered section. The tapered section is located at a distal portion of the flexible elongate member and has a first wall subsection having a uniform thickness and a second wall subsection having a thickness larger than the uniform thickness. The second subsection flexes to maintain circumferential contact with the phaco tip.

In another exemplary aspect, the present disclosure is directed to a surgical system. The surgical system includes a handheld device that couples a control system to an elongate material-removal component and a flexible sleeve covering an extended portion of the material-removal component. The material removal component has a first radius. The flexible sleeve exposes a distal end of the material-removal element and has a lumen extending therethrough. The lumen has a second radius that is larger than the first radius so as to permit an irrigation fluid to flow between the material-removal component and the sleeve. A distal end of the flexible elongate member includes a flexible contact portion that maintains circumferential contact with the material-removal component.

In another exemplary aspect, the present disclosure is directed to a method of performing a procedure within an eye of a patient. The method includes steps of forming an incision in an outer tissue of the eye of the patient for insertion of a phaco tip and of positioning a flexible sleeve over the phaco tip. The distal end of the flexible sleeve includes a flexible contact portion that maintains circumferential contact with the material-removal component. The method also includes steps of flowing an irrigation fluid between the phaco tip and the flexible sleeve, the irrigation fluid exiting at least one port in the flexible sleeve near the distal end of the flexible sleeve, and of removing material from within the eye of the patient using the phaco tip.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

FIG. 2 is a cross-sectional illustration of an exemplary surgical hand piece having a phacoemulsification tip.

FIGS. 3A, 3B, 3C, and 3D are close-up end views of a distal portion of the phacoemulsification tip of FIG. 2 under various conditions.

FIGS. 6A and 6B are close-up cross-sectional illustrations of different embodiments of distal portions that may form a part of the infusion sleeve of FIG. 5A, each having an aspiration tube positioned therein, according to exemplary aspects of the present disclosure.

FIGS. 8A and 8B are cross-sectional illustrations of a distal portion of an infusion sleeve in two different pressure conditions according to exemplary aspects of the present disclosure.

Figure 1:
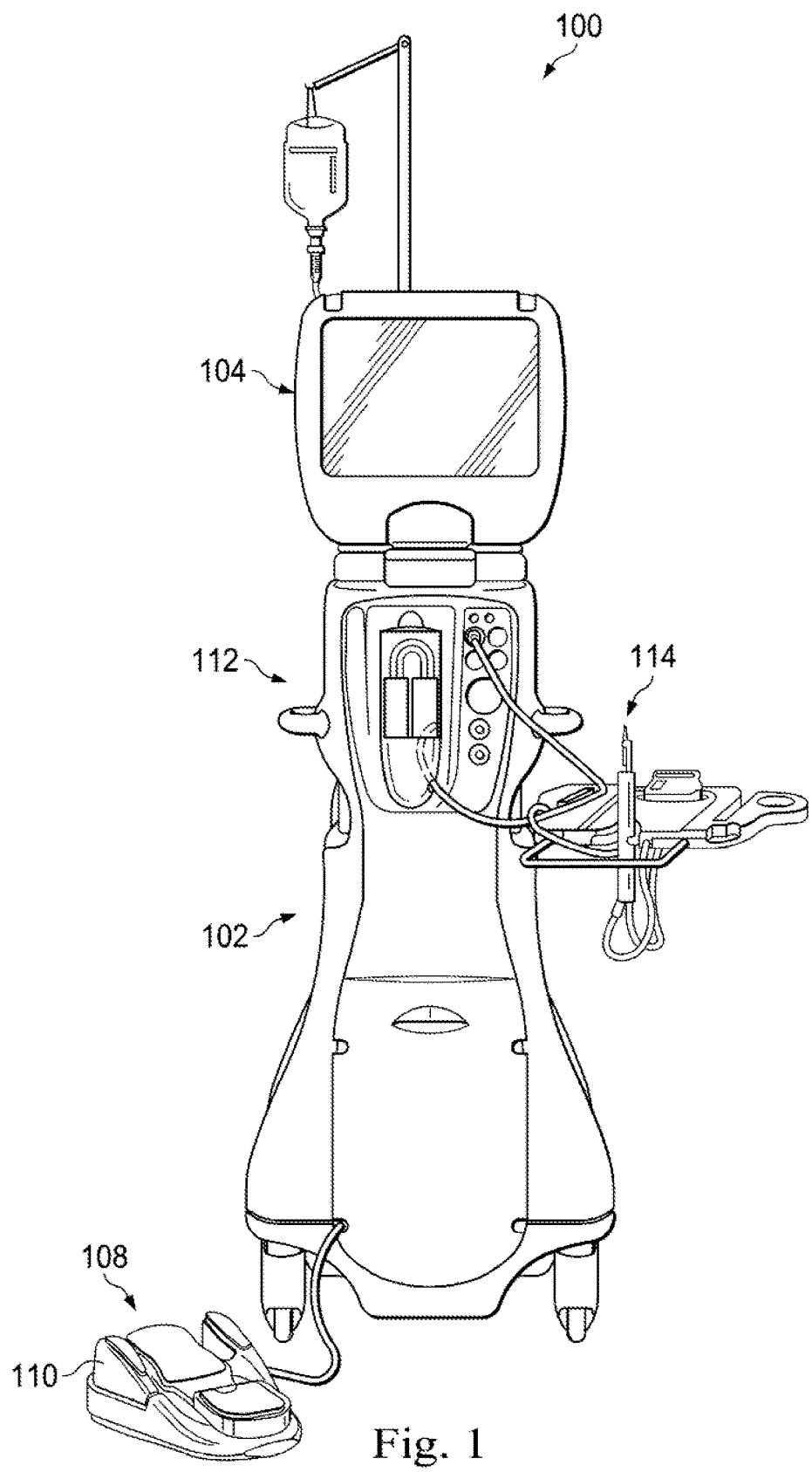
FIG. 1 is an illustration of an exemplary phacoemulsification surgical console according to one aspect of the present invention implementing the teachings and principles described herein.

These figures are better understood by reference to the following detailed description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems and methods for impeding the forward flow of irrigating fluid from an irrigating or infusion sleeve during ophthalmic surgery, particularly surgeries in which the surgeon needs to remove portions of a lens from a patient's eye, such as a cataract surgery. By reducing the forward flow during operation, surgical efficiency may be increased and clinical outcomes may be improved. Forward flow is to be reduced by maintaining circumferential contact between a distal end of an infusion sleeve and an aspiration tube running therethrough. The contact is maintained so as to permit a degree of independent rotation between the infusion sleeve and the aspiration tube so as to prevent twisting of the infusion sleeve during operation.

FIG. 1 illustrates an exemplary emulsification surgical system, shown as a console, generally designated 100. The console 100 includes a base housing 102 with a computer unit 104 and an associated display screen adapted to show data relating to system operation and performance during an emulsification surgical procedure. The console 100 also includes a number of subsystems that may be used together to perform a phacoemulsification surgical procedure. For example, the subsystems may include one or more of a foot pedal subsystem 108 including a foot pedal 110 having a number of foot actuated controls, a fluidics subsystem 112 including a hand-held surgical instrument shown as hand piece 114. The console 100 further includes an ultrasonic generator subsystem within the housing 102 that is operable to cause a phaco tip of the hand piece 114 to oscillate ultrasonically. Some embodiments of the console 100 further include a pneumatic vitrectomy cutter subsystem with a vitrectomy hand piece. These subsystems of console 100 may overlap and cooperate to perform various aspects of a procedure and may be operable separately and/or independently from each other during one or more procedures. That is, some procedures may utilize one or more subsystems while excluding others.

FIG. 2 shows a cross-section of the hand piece 114 in greater detail. Referring to FIG. 2, the hand piece 114 includes an irrigation conduit 202 in communication with a sleeve 204 and includes an aspiration conduit 206 in communication with an elongate material-removal component 208. An enlarged portion of the sleeve 204 may extend over a distal end of a housing of the hand piece 114. As can be seen, the elongate material-removal component 208 or the phaco tip 208 extends through the sleeve 204 to define an annular space 210. The irrigation conduit 202 provides irrigating fluid through the annular space 210 and the aspiration conduit 206 transports fluid and emulsified particles from a lumen 212 of the phaco tip 208 to an aspiration system, included in the console 100 of FIG. 1, during the surgical procedure.

The hand piece 114 also includes a pressure sensor 214. The pressure sensor 214 is disposed in the hand piece 114 along the irrigation conduit 202. Although shown at the proximal end of the hand piece 114, in other embodiments, the pressure sensor 214 may be disposed at the distal end and in some instances may be disposed proximate the sleeve 204. Further detail regarding an embodiment of the hand piece 114 may be found in U.S. Provisional Patent Application Ser. No. 61/774,359 entitled "Active Acoustic Streaming in Hand Piece for Occlusion Surge Mitigation", filed Mar. 7, 2013, whose inventors are Satish Yalamanchili which is hereby incorporated by reference in its entirety as though fully and completely set forth herein. The hand piece 114 may further include aspects of the ultrasonic generator subsystem of the console 100 of FIG. 1. While FIG. 2 illustrates a hand piece 114 with a bent phaco tip 208, other embodiments of the hand piece 114 include a straight phaco tip 208.

FIGS. 3A, 3B, 3C, and 3D are end views that provide additional detail regarding the distal portion of the hand piece 114 as seen in FIG. 2 and discussed above. Particularly the views depict the sleeve 204, the phaco tip 208, the annular space 210 and the lumen 212 that runs through the phaco tip 208. The lumen 212 couples to the aspiration conduit 206 to transport fluid and emulsified particles during the surgical procedure. As illustrated in FIG. 3A, the phaco tip 208 is aligned coaxially with the sleeve 204 such that the annular space 210 exhibits a consistent separation distance. As depicted, the phaco tip 208 and the sleeve 204 may be considered well matched in size.

As illustrated in FIG. 3B, the phaco tip 208 and the sleeve 204 are misaligned, such that they are no longer coaxially positioned. Such a configuration may occur more regularly in embodiments of the hand piece 114 in which the phaco tip 208 is a bent tip. While the flexibility of sleeve 204 may accommodate such a bend, the alignment may still be other than coaxial. As can be seen in FIG. 3B, the annular space 210 may be greater on the top than on the bottom as illustrated. This may result in additional forward flow at the top than is desirable.

FIGS. 3C and 3D illustrate a configuration of a sleeve 204 and a phaco tip 208 that are less similar in size than those depicted in FIGS. 3A and 3B. Thus, the annular space 210 may allow for more undesirable forward flow than the sleeve 204 and tip 208 in FIGS. 3A and 3B. Unlike in FIG. 3C, in which the phaco tip 208 and the sleeve 204 are generally coaxially aligned, in FIG. 3D there is significant non-uniformity in the annular space 310. As discussed above, this may increase forward flow and/or add a degree of directionality to the forward flow of the configuration shown in FIG. 3D.

Figure 4:
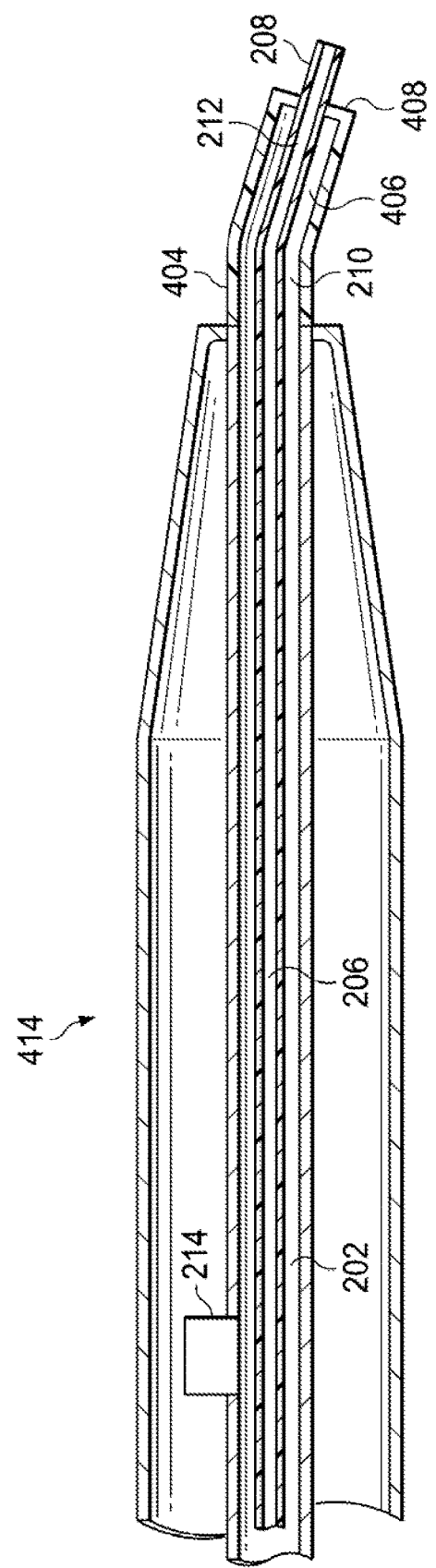
FIG. 4 is a cross-sectional illustration of an exemplary surgical hand piece having a phacoemulsification tip according to exemplary aspects of the present disclosure.

FIG. 4 illustrates a cross-sectional view of an alternative hand piece 414. This hand piece 414 shared many of the same features and qualities as described above with respect to the hand piece 114 as included in FIGS. 1 and 2. Hand piece 414 is used in embodiments of console 100 in the performance of associated surgical procedures. Hand piece 414 includes an irrigation conduit 202 in communication with an irrigation or infusion sleeve 404 and includes an aspiration conduit 206 in communication with a phaco tip 208. The phaco tip 208 may have an external diameter ranging from about 0.028 inches to about 0.036 inches. As can be seen, the phaco tip 208, which has a lumen 212 extending therethrough, extends through the sleeve 404 to define an annular space 210. The hand piece 414 also includes a pressure sensor 214.

The sleeve 404 shares many features with the sleeve 204 discussed above. The sleeve 404 includes a flexible elongate portion with a central, generally cylindrical lumen 406 that extends therethrough. When the sleeve 404 is positioned over the phaco tip 208, the phaco tip 208 and the cylindrical lumen 406 form the annular space 210 through which irrigating fluid flows. The sleeve 404 may be made from silicone, or any other flexible, biocompatible material or biocompatible-coated material. The sleeve 404 includes a distal end 408 that differs from that of the sleeve 204 of FIGS. 2 and 3A-D in some respects. The distal end provides a contacting ring that contacts an inserted phaco tip. More detail is provided regarding the distal end 408 in FIGS. 5A-D. A proximal end of the sleeve 404 may abut a housing of the hand piece 414 as illustrated in FIG. 4. In other embodiments, the sleeve 404 includes an enlarged proximal portion (not depicted) that conformingly extends over an adjacent, distal portion of the housing of the hand piece 414. The enlarged proximal portion may serve to secure the sleeve 404 to the hand piece 414 and seal the proximal end of the sleeve 404 so that fluid does not leak backward. Because the sleeve 404 is flexible, it may conform to a shape of an inserted phaco tip, whether straight or bent as illustrated in FIG. 4.

Figure 5C:
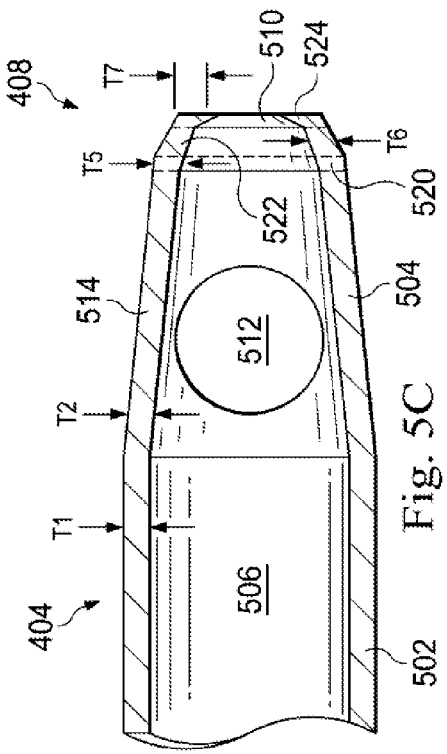
FIGS. 5B, 5C, and 5D are close-up cross-sectional illustrations of different embodiments of distal portions that may form a part of the infusion sleeve of FIG. 5A according to various exemplary aspects of the present disclosure.
Figure 5D:
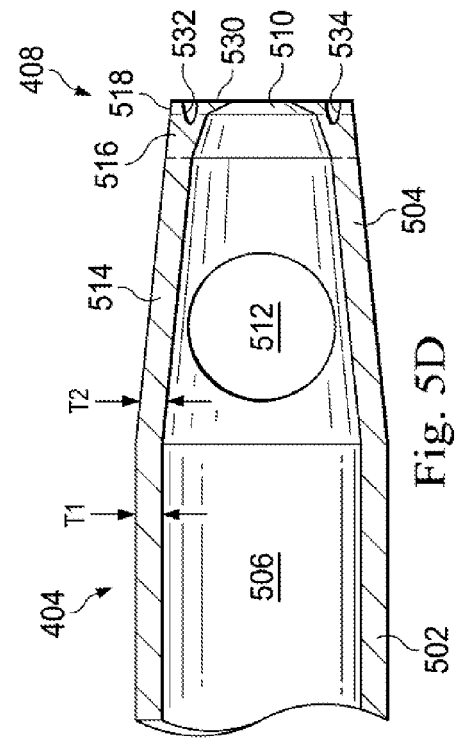
Figure 5A:
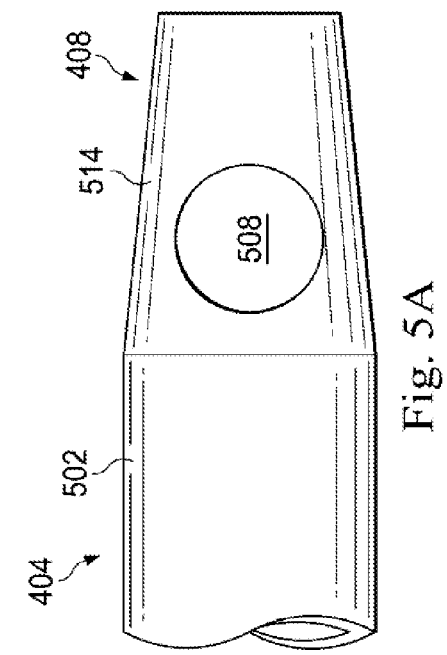
FIG. 5A is a close-up illustration of a distal portion of the infusion sleeve of FIG. 4 according to exemplary aspects of the present disclosure.

FIG. 5A shows additional detail regarding the distal portion of the sleeve 404 of FIG. 4, including the distal end 408 thereof. As illustrated in FIG. 5A, and in associated FIGS. 5B, 5C, and 5D, the sleeve 404 is depicted as separate from a phaco tip 208 to simplify the disclosure. FIG. 5A illustrates a non-cross-sectional view and so depicts a straight section 502 of the flexible elongate portion of sleeve 404. The straight section has a generally constant thickness or diameter along its length. A tapered section 504 abuts the straight section 502. A lumen 506, depicted in the cross-sectional views of FIGS. 5B-D, extends through both the straight section 502 and the tapered section 504. The lumen 506 may have a constant diameter through the straight section 502, while having a decreasing diameter through the tapered section 504. The decreasing diameter of the lumen 506 as it extends through the tapered section 504 may be such that a thickness of the tapered section is constant over a length of the tapered section 504. Also included in FIG. 5A is a first port 508. The first port 508 is an opening in the flexible elongate portion of the sleeve 404. While the first port 508 may be present in the straight section 502, in the illustrated embodiment the first port 508 is formed in the tapered section 504. Other embodiments may include additional ports on either or both the tapered section 504 and the straight section 502 near the distal end 408 of the sleeve 404.

Figure 5B:
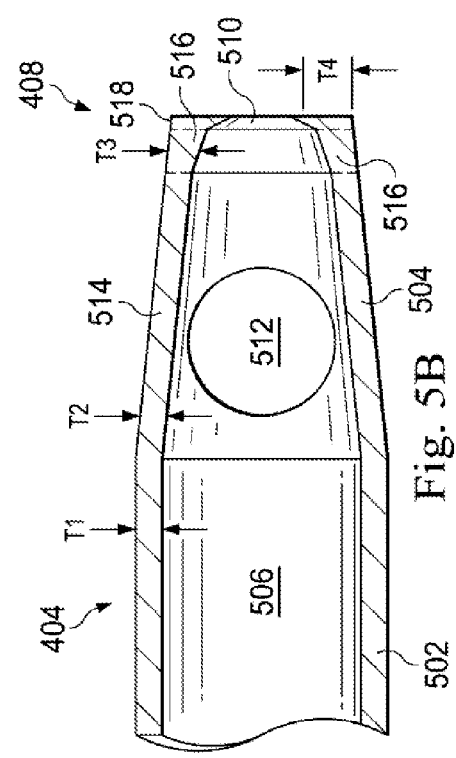

FIGS. 5B, 5C, and 5D are cross-sectional illustrations of the sleeve 404 as depicted in FIGS. 4 and 5A. As depicted in FIG. 5B, the straight section 502 has a generally constant thickness T1. For example, the straight section 502 may have a thickness T1 of about 0.003 inches. The tapered section 504 also has a generally constant thickness T2, which may be the same or different from the thickness T1 of the straight section 502. In the example shown, the tapered section 504 exhibits a uniform external tapering, such that the degree of tapering remains constant throughout the section 504. FIG. 5B more clearly illustrates the lumen 506 into which a phaco tip 208 may be inserted as depicted in FIG. 4. When in place, the phaco tip 208 of FIG. 4 extends out of the lumen 506 through an opening 510. The sleeve 404 of FIG. 5B also includes a second port 512 that forms an opening in the sleeve 404 through which irrigating fluid may exit the lumen 506 or the annular space 210 when a phaco tip 208 is present. The port 512 opens in a direction transverse to the direction of the opening 510. Thus, as depicted, the sleeve 404 includes a first port 508 and a second port 512 disposed opposite each other on the tapered section 504.

As illustrated in FIG. 5B, the tapered section 504 includes a plurality of wall subsections at a distal end thereof. The depicted embodiment includes a first wall subsection 514, a second wall subsection 516, and a third wall subsection 518. The first subsection 514 of the tapered section 504 has the substantially uniform thickness T2. The second subsection 516 has an increasing thickness T3, with the thickness T3 increasing from a proximal end of the subsection 516 to a distal end thereof. As illustrated, the tapered section 504 further includes a third section 518 that has an increasing thickness T4 that increases toward a distal end thereof. In some embodiments of the tapered section 504, the thickness T3 and T4 correspond such that the second and third sections 516 and 518 form a continuous subsection. While the thicknesses T3 and T4 are illustrated as increasing linearly toward a distal end of the sleeve 404, in other embodiments the increase may be characterized by a curve. Additionally, some embodiments of the sleeve 404 include a thickness T2 of the first subsection 514 that either increases in thickness or decreases in thickness in proximity to the distal end 408. Other embodiments of the sleeve 404 may include yet more wall subsections having thicknesses that increase or decrease in proximity to the distal end 408 and the opening 510. As depicted, the thickness T4 is generally greater than the thickness T3, which in turn is generally greater than the thickness T2.

The thicknesses T2, T3, and T4 are selected to provide for additional flexibility in the tapered section 504 as it circumferentially contacts a phaco tip 208. For example, in some embodiments the thickness T2 is not a uniform thickness, and the subsection 514 decreases in thickness with proximity to the distal end 408. The subsections 514, 516, and 518 may also have different lengths in other embodiments. For example, the subsection 516 may begin closer to the ports 508 and 512. This and other embodiments will be discussed in greater detail below.

FIG. 5C presents an alternative cross-sectional view of embodiments of the sleeve 404 of FIGS. 4 and 5A. In FIG. 3C, the tapered section 504 includes four wall subsections: subsection 514, subsection 520, subsection 522, and subsection 524. These subsections have corresponding thicknesses T2, T5, T6, and T7, respectively. The interior profile formed by the subsections 520-524 is substantially the same as the interior profile formed by subsections 516 and 518 of FIG. 5B. However, in addition to a decreasing diameter of the lumen 506 corresponding to the increasing thicknesses T3 and T4, the geometries of subsections 520-524 are such that the uniform external tapering of the tapered section 514 is altered beginning at the subsection 522. Thereafter an exterior surface of the tapered section 514 exhibits a higher degree of tapering.

FIG. 5D also presents an alternative cross-sectional view of the sleeve 404 of FIGS. 4 and 5A. As illustrated, the sleeve 404 of FIG. 5D shares many of the features of the sleeve 404 of FIG. 5B as described above. The tapered section 504 of FIG. 5D includes the first subsection 514, the second subsection 516, and the third subsection 518. The sleeve 404 as illustrated in FIG. 5D further includes a plurality of recesses or pockets formed in a distal face 530 of the sleeve 404. As illustrated, the sleeve 404 includes a first pocket 532 and a second pocket 534. The pockets may be formed during a molding process used to create the sleeve 404, or may be formed by the subsequent removal of material.

The various thicknesses and taperings present in the various wall subsections of the tapered section 504 described above in connection with FIGS. 5A-5D may be combined in a number of manners. These features may permit a circumferential contact between the distal end 408 of the sleeve 404 with an inserted phaco tip 208 that impedes forward flow out of the distal opening 510 while the phaco tip 208 ultrasonically vibrates. By "impeding", it is meant that a forward flow is resisted or stopped by the distal end 408. The surface area of the contact between the sleeve 404 and the phaco tip 208 may also be decreased by the configuration of the subsections so that the phaco tip 208 and the sleeve 404 may rotate coaxially without causing twisting that may impede flow through the ports 508 and/or 512. The distal end 408 of a sleeve 404 may be sufficiently rigid to prevent forward flow, but flexible enough so that a single sleeve 404 may accommodate a variety of phaco tip sizes and configurations. In some embodiments, the first and second pockets 532 and 534 may be a part of an annular ring pocket extending about the opening 510. Pockets, like the first and second pockets 532 and 534 may permit more flexible contact between the distal end 408 of the sleeve 404 and the phaco tip 208.

FIG. 6A illustrates a partial cross-sectional view of a sleeve 404 (shown in cross-section) having a phaco tip 208 (not shown in cross-section) inserted through the central lumen 506 (thereby forming the annular space 510) and extending beyond the opening 510. As discussed above, the different thicknesses and taperings in embodiments of sleeve 404 of FIGS. 4 and 5A-D may permit circumferential contact between the distal end 408 of the sleeve 404 and the inserted phaco tip 208. As depicted in FIG. 6A, the phaco tip 208 includes an external diameter D1. This external diameter D1 causes an amount of flexing in the subsections of the tapered section 504 close to or at the distal end 408.

FIG. 6B also illustrates partially cross-sectioned view of a sleeve 404 (shown in cross-section) having a phaco tip 208 (not shown in cross-section) inserted through the central lumen 506 as in FIG. 6A. However, the external diameter D2 of the phaco tip 208 in FIG. 6B is smaller than the external diameter D1 as illustrated in FIG. 6A. For example, the phaco tip 208 in FIG. 6B may have an external diameter of about 0.7 millimeters. Because the external diameter D2 is smaller than the external diameter D1, an amount flexing caused in the subsections of the tapered section 504 may be less than the amount of flexing illustrated in FIG. 6A.

As illustrated in FIGS. 6A and 6B, a given sleeve 404 may accommodate phaco tips having a wider range of external diameters. Across a range of external diameters, the sleeve 404 maintains circumferential contact with the phaco tip 208 in such a way that a degree of independent rotation is permitted, thereby avoiding or decreasing twisting in the sleeve 404.

Figure 7A:
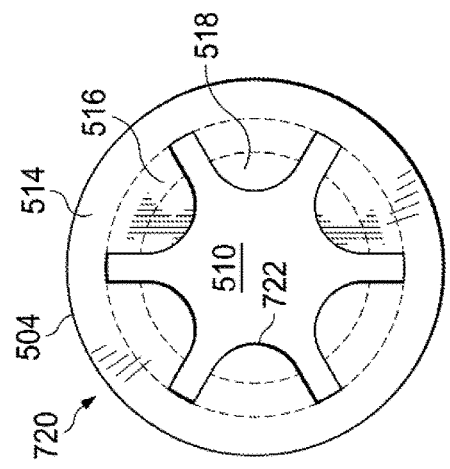
FIGS. 7A, 7B, 7C, 7D, and 7E are a plurality of close-up illustrations of different embodiments of distal ends of infusion sleeves according to exemplary aspects of the present disclosure.
Figure 7B:
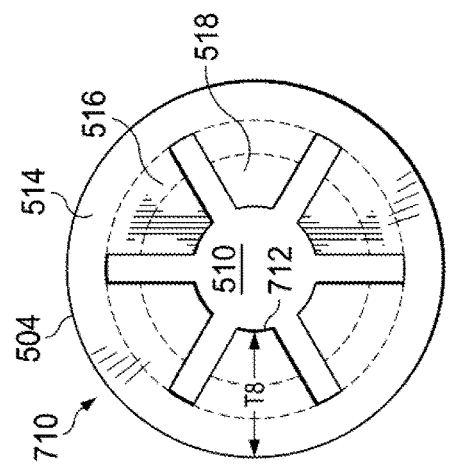
Figure 7C:
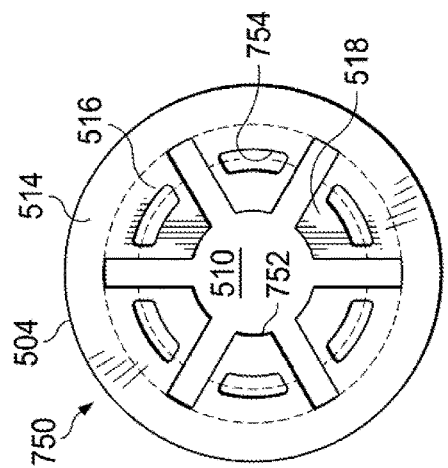
Figure 7D:
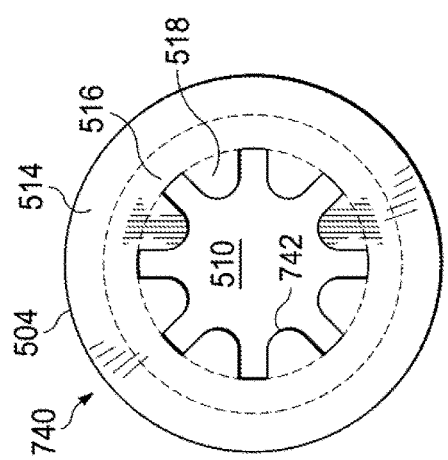
Figure 7E:
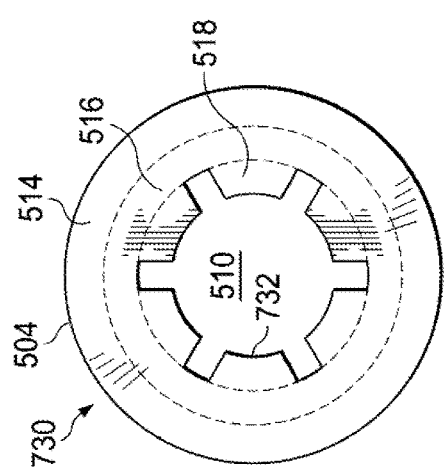

FIGS. 7A-E show a number of end views of different embodiments of the distal face 530 as discussed in connection with FIG. 5D above. The distal face of a sleeve 404 may be similar to the illustrated faces of FIG. 7A-E. FIG. 7A shows a distal face 710 that includes a plurality of contacting flaps, such as an exemplary flap 712. The flap 712 includes straight sides, such that the flap 712 is generally trapezoidal. As depicted, the flap 712 is formed by the removal of some material from both subsection 516 and subsection 518. In some embodiments, the flap 712 has a thickness T8 of about 0.008 inches, though other embodiments have thicker or thinner flaps. In FIG. 7B, a distal face 720 includes a plurality of rounded flaps, like an exemplary flap 722. Like the flaps of distal face 710, the plurality of rounded flaps is formed by the removal of material from both subsections 516 and 518. Distal faces 730 and 740, shown in FIGS. 7C and 7D are similar to distal faces 710 and 720, respectively. However, as illustrated in FIG. 7C, an exemplary flap 732 includes material removed from subsection 518, but not 516. An exemplary flap 742 of FIG. 7D differs from the exemplary flap 722 in the same manner. FIG. 7E shows a distal face 750 that is similar in many respects to the distal face 710. However, an exemplary flap 752 on the distal face 750 further includes a pocket 754. The pocket 754 may be formed by the removal of a portion of material from the distal face 750 as described in relation to the pockets 532 and 534 in FIG. 5D. The pocket 754 may permit the flap 752 to bend more easily. The flaps may vary in size, shape, and numbers.

Combinations of the various aspects of these faces may be used in embodiments of the distal face of sleeve 404. The flaps may vary in size, shape, and numbers. For example, rounded flaps with pockets may be formed in a distal face. The flaps may permit periodic circumferential contact between a sleeve 404 and a phaco tip 208, with a contact being made at each flap. Additionally, some embodiments of the distal face may not include flaps. Such embodiments may provide continuous circumferential contact between a sleeve 404 and a phaco tip 208. Such embodiments may contact periodically positioned pockets, like pocket 754, on a distal face thereof or may contain a single annular pocket to enhance the flexibility of the distal end of the sleeve. The distal face may be configured to facilitate the accommodation of phaco tips of varying sizes and shapes.

FIGS. 8A and 8B illustrate a sleeve 800 that is configured with relief valves 802 and 804. As depicted, the sleeve 800 includes a phaco tip 208 inserted therethrough, thus forming an annular space 810 through which an irrigation fluid is flowing as indicated by the fluid paths A1 and A2. In FIG. 8A, the irrigation fluid exits the annular space 810 through a first port 812 and a second port 814 along fluid paths. The ports 812 and 814 are openings, disposed opposite each other, in a wall of the sleeve 800 to provide an exit route for the irrigation fluid. FIG. 8A depicts the sleeve 800 in a condition in which the pressure exerted by the irrigation fluid is below a threshold.

FIG. 8B depicts the sleeve 800 in a condition in which the pressure is above a threshold. The threshold is provided by a physical configuration of the relief valve 802 and 804. Below the threshold, the valves 802 and 804 are compressed or pinched closed. The valves 802 and 804 may be provided by slits in the tapered section or the straight section of the sleeve 800. Due to the flexible, elastic properties of the material from which the sleeve 800 is fabricated, the valves 802 and 804 remain closed until the threshold is exceeded, in which case the valves 802 and 804 provide additional outlets for the irrigation fluid, reconfiguring the fluid paths A1 and A2 of FIG. 8A into the fluid paths B1 and B2 of FIG. 8B. By providing the relief valves 802 and 804, a temporary increase in pressure may not increase forward flow out of the distal end of the sleeve 800. Rather, the additional outlets through which irrigation fluid flows in fluid paths B1 and B2 may direct fluid away from the distal end of sleeve 800.

Figure 9:
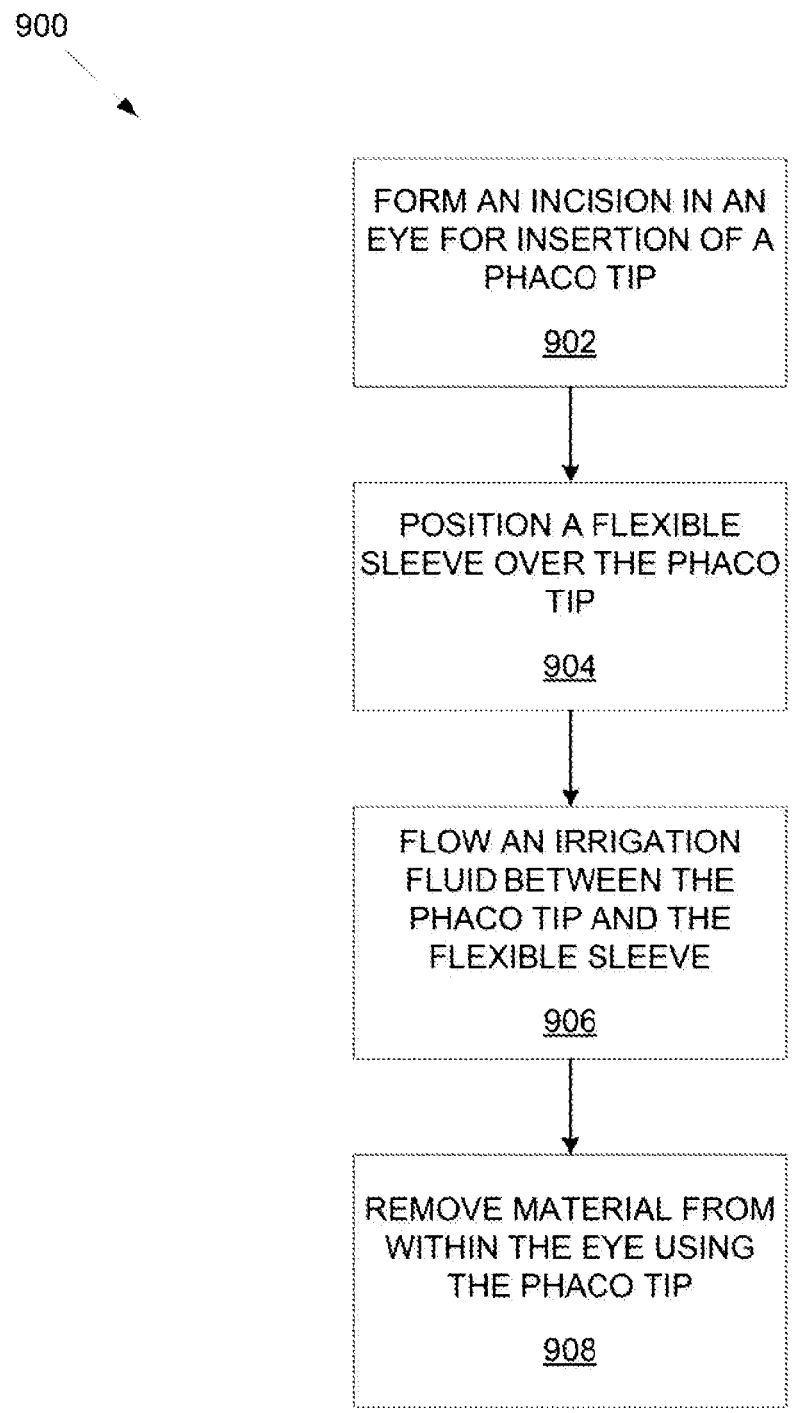
FIG. 9 is a flowchart showing a method of performing a procedure within an eye of a patient according to exemplary aspects of the present disclosure.

FIG. 9 is a flowchart of a method 900 of performing a procedure within an eye of a patient. The method 900 is depicted as including a plurality of enumerated steps. However, embodiments of the method 900 may include additional steps before, after, or in between the enumerated steps. In step 902, a surgeon forms an incision in an outer tissue of the eye of the patient for insertion of a phaco tip, such as that depicted in FIG. 4. For example, the incision may be formed in a cornea of the patient to permit access into the anterior chamber to provide access to the lens of the patient.

In step 904, in preparation for the insertion of the phaco tip, the surgeon or a technician positions a flexible sleeve over the phaco tip. A distal end of the flexible sleeve includes a flexible contact portion that maintains circumferential contact with the phaco tip. Sleeves described herein may be used in step 904. For example, a sleeve 404 may be used with a distal end 408 as shown in FIG. 5D and with a distal face 750 as shown in FIG. 7 may be placed over a phaco tip 208. In some embodiments, step 904 may be performed prior to step 902.

In step 906, a console may begin to flow an irrigation fluid between the phaco tip and the flexible sleeve, with the irrigation fluid exiting at least one port in the flexible sleeve near the distal end of the flexible sleeve. For example, the console 100, which includes a fluid reservoir and associated pumps, may pump irrigation fluid through the annular space of the hand piece 404. The irrigation fluid may cool the phaco tip 208 and provide a medium by which the emulsified material may be removed by the aspiration conduit 206 through the phaco tip 208. The irrigation fluid exits a port or ports, like port 508 and 512 illustrated in FIGS. 5A and 5B or ports 812 and 814 in FIGS. 8A and 8B. When a pressure exerted by the irrigation fluid exceeds a threshold, relief valves 802 and 804 may open to allow more irrigation fluid to exit the sleeve 404.

In step 908, the aspiration conduit 206, running through the hand piece 414 and the phaco tip 208 allows the surgeon to remove material from within the eye of the patient using the phaco tip. Portions of the emulsified material may be suspended in the irrigation fluid and then pulled through the aspiration conduit 206 along with the irrigation fluid.

The systems and methods disclosed herein may be used to provide better performance of phaco tips and associated surgical systems by impeding or preventing the forward flow of irrigation fluid out of a distal end of the infusion sleeve by maintaining circumferential contact between the tip and the sleeve. This may be done while also allowing the infusion sleeve and the phaco tip to be rotated independently to prevent or decrease the effects of twisting, which can adversely impact the exit of irrigation fluid out of ports in the sleeve. This may result in more efficient and effective treatment of patients, thereby improving the overall clinical result. Additionally, a single infusion sleeve may be provided that accommodates phaco tips of differing sizes, providing potential cost savings as well.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An infusion sleeve for partially covering a phacoemulsification tip usable during a surgical operation, the infusion sleeve comprising:
   a flexible elongate portion having a lumen extending therethrough from a proximal end to a distal end, the lumen being configured to receive the phacoemulsification tip therethrough, the flexible elongate portion including:
      at least one lateral port configured on a side of the flexible elongate portion and in communication with the lumen;
      a straight section; and
      a tapered section adjacent the straight section and located at a distal portion of the flexible elongate portion, wherein the tapered section comprises a first wall subsection having a uniform thickness and a second wall subsection having thickness larger than the uniform thickness, the second wall subsection being configured to flex and maintain circumferential contact with the phacoemulsification tip during a phacoemulsification procedure.

2. The infusion sleeve of claim 1, wherein the second wall subsection comprises a contacting ring that maintains continuous circumferential contact with the phacoemulsification tip while the phacoemulsification tip ultrasonically vibrates.

3. The infusion sleeve of claim 1, wherein the second wall subsection comprises a plurality of contacting flaps, the plurality of contacting flaps being configured to maintain circumferential contact along spaced segments of the phacoemulsification tip while the phacoemulsification tip ultrasonically vibrates.

4. The infusion sleeve of claim 3, wherein each contacting flap has a pocket of removed material, the pocket of removed material increasing bending flexibility of the contacting flap in a manner accommodating the phacoemulsification tip.

5. The infusion sleeve of claim 3, wherein each flap of the plurality of contacting flaps has a rectangular face or a rounded face.

6. The infusion sleeve of claim 1, wherein the tapered section further comprises a third wall subsection between the first wall subsection and the second wall subsection, the third wall subsection having a thickness that increases with proximity to a distal end of the tapered section.

7. The infusion sleeve of claim 6, wherein a thickness of the second wall subsection increases along an axial length in a direction of the distal end with proximity to the distal end of the tapered section, the second wall subsection increasing in thickness more rapidly than the third wall subsection.

8. The infusion sleeve of claim 1, wherein the at least one port comprises a first port and second port disposed on opposing sides of the tapered section, the first and second ports configured to permit an irrigation fluid to exit the infusion sleeve.

9. The infusion sleeve of claim 1, wherein the tapered section further comprises at least one surge release valve configured to permit an irrigation fluid to flow when a pressure within the tapered section increases above a threshold.

10. A phacoemulsification surgical system comprising:
a handheld device that couples a control system to an elongate material-removal component, the material removal component having a first radius; and
a flexible sleeve covering a portion of the material-removal component while exposing a distal end of the material-removal component, the flexible sleeve having a lumen therethrough, the lumen having a second radius that is larger than the first radius so as to permit an irrigation fluid to flow between the material-removal component and the sleeve, wherein a distal end of the flexible sleeve includes a flexible contact portion having a plurality of contacting flaps that maintains at least partial circumferential contact with the material-removal component along spaced segments of the material-removal component while the material-removal component ultrasonically vibrates.

11. The surgical system of claim 10, wherein the flexible sleeve includes a proximal portion configured to partially cover a distal portion of the handheld device.

12. The surgical system of claim 10, wherein the material-removal component is a phacoemulsification tip.

13. The surgical system of claim 10, wherein the flexible contact portion impedes the irrigation fluid from flowing out the distal end of the flexible sleeve.

14. The surgical system of claim 10, wherein the flexible sleeve comprises:
a proximal end; and
at least two irrigation ports disposed near the distal end of the flexible sleeve that permit the irrigation fluid entering in the proximal end of the flexible sleeve to exit the flexible sleeve near the distal end.

15. The surgical system of claim 10, wherein the elongate material-removal component has a bend, the flexible sleeve conforming to the bend.

16. The surgical system of claim 10, wherein the circumferential contact permits rotation of the material-removal component within the flexible sleeve and impedes the irrigation fluid from flowing out the distal end of the flexible sleeve.

17. The surgical system of claim 10, wherein the elongate material-removal component is a bent phacoemulsification tip.

18. A method of performing a procedure within an eye of a patient, the method comprising:
forming an incision in an outer tissue of the eye of the patient for insertion of a phacoemulsification tip;
positioning a flexible sleeve over the phacoemulsification tip, a distal end of the flexible sleeve including a flexible contact portion having a plurality of contacting flaps that maintains contact with a material-removal component while the material-removal component is used in the procedure;
flowing an irrigation fluid between the material-removal component and the flexible sleeve, the irrigation fluid exiting at least one port in the flexible sleeve near the distal end of the flexible sleeve; and
removing material from within the eye of the patient using the material-removal component.

19. The method of claim 18, further comprising impeding a flow of the irrigation fluid out of the distal end of the flexible sleeve.

20. The method of claim 18, wherein the flexible sleeve is formed from silicone.

* * * * *